US 7,528,959 B2

(12) United States Patent
Novotny et al.

(10) Patent No.: US 7,528,959 B2
(45) Date of Patent: May 5, 2009

(54) APPARATUS AND METHOD FOR SIZING NANOPARTICLES BASED ON INTERFEROMETRIC FIELD DETECTION

(75) Inventors: Lukas Novotny, Rochester, NY (US); Filipp Ignatovich, Rochester, NY (US)

(73) Assignee: University of Rochester, Rochester, NY (US)

(*) Notice: Subject to any disclaimer, the term of this patent is extended or adjusted under 35 U.S.C. 154(b) by 0 days.

(21) Appl. No.: 12/041,873

(22) Filed: Mar. 4, 2008

(65) Prior Publication Data
US 2008/0218766 A1 Sep. 11, 2008

Related U.S. Application Data

(63) Continuation of application No. 11/417,254, filed on May 4, 2006.

(60) Provisional application No. 60/677,411, filed on May 4, 2005.

(51) Int. Cl.
*G01B 11/02* (2006.01)
(52) U.S. Cl. .................................... 356/496
(58) Field of Classification Search ............. 356/28.5, 356/511, 456, 496
See application file for complete search history.

(56) References Cited

U.S. PATENT DOCUMENTS

| 4,477,187 | A |   | 10/1984 | Pettit et al. |
| 4,886,360 | A |   | 12/1989 | Finlan et al. |
| 4,964,726 | A |   | 10/1990 | Kleinknecht et al. |
| 5,037,202 | A | * | 8/1991  | Batchelder et al. .......... 356/336 |
| 5,133,602 | A | * | 7/1992  | Batchelder et al. .......... 356/615 |
| 5,621,523 | A |   | 4/1997  | Oobayashi et al. |
| 5,978,083 | A |   | 11/1999 | Muller et al. |
| 6,061,070 | A |   | 5/2000  | Sugaya |
| 6,549,801 | B1|   | 4/2003  | Chen et al. |
| 6,833,923 | B2| * | 12/2004 | Florin et al. ................. 356/601 |
| 2002/0167672 | A1 | * | 11/2002 | Anezaki et al. ............. 356/458 |
| 2003/0124516 | A1 | * | 7/2003  | Chung et al. .................... 435/5 |
| 2004/0263858 | A1 |   | 12/2004 | Song et al. |
| 2005/0036151 | A1 |   | 2/2005  | Gornick et al. |
| 2005/0073681 | A1 |   | 4/2005  | Sevick-Muraca et al. |
| 2005/0128488 | A1 |   | 6/2005  | Yelin et al. |
| 2005/0168753 | A1 |   | 8/2005  | Butt et al. |
| 2007/0030492 | A1 |   | 2/2007  | Novotny et al. |
| 2007/0206203 | A1 | * | 9/2007  | Trainer ....................... 356/521 |

FOREIGN PATENT DOCUMENTS

WO    WO-03/106956    12/2003

OTHER PUBLICATIONS

International Preliminary Report on Patentability in corresponding International application No. PCT/US2007/005002.

* cited by examiner

*Primary Examiner*—Michael A Lyons
*Assistant Examiner*—Scott M Richey
(74) *Attorney, Agent, or Firm*—Blank Rome LLP

(57) ABSTRACT

Light from a laser source is split into a reference arm and a detection arm. The light in the detection arm is focused into a channel containing particles to be detected and is backscattered by the particles. The light in the reference arm is attenuated. The attenuated and backscattered light are caused to interfere and detected by a split detector so that the effects of background light can be subtracted out, while the backscattered light is detected to detect the particles.

8 Claims, 3 Drawing Sheets

APPARATUS AND METHOD FOR SIZING NANOPARTICLES BASED ON INTERFEROMETRIC FIELD DETECTION

REFERENCE TO RELATED APPLICATION

The present application is a continuation of U.S. patent application Ser. No. 11/417,254, filed May 4, 2006, now pending, which claims the benefit of U.S. Provisional Patent Application No. 60/677,411, filed May 4, 2005, whose disclosures are hereby incorporated by reference in their entirety into the present disclosure.

STATEMENT OF GOVERNMENT INTEREST

The work leading to the present invention was supported by NSF Grant No. PHS-0441964 and DARPA Grant No. MDA972-00-1-0021. The government has certain rights in the invention.

FIELD OF THE INVENTION

The present invention is directed to a technique for the detection of nanoparticles, such as viruses, and more particularly to an optical technique using interferometry which lessens the dependence on particle radius relative to known techniques.

DESCRIPTION OF RELATED ART

Particles with characteristic sizes of less than 100 nm are becoming increasingly important in the context of nanoscience and technology. Applications range from solid-state physics to biology. For example, semiconductor nanoparticles are used as single photon emitters in quantum information science and as fluorescent markers for biological processes. Similarly, noble metal particles are used as contrast agents in microscopy, as biochemical sensors, as probes in scanning probe microscopy, or as nonbleachable biological labels. Furthermore, specially engineered particles such as nanoshells are employed for photo-thermal tumor ablation and for cancer therapies. Polymer nanoparticles are being used as calibration standards and, in functionalized form, also as probes in biological imaging. There are also various naturally occurring nanoparticles of high societal impact. Among them are carbon particles originating from combustion or different sorts of infectious viruses.

Because of their small size, nanoparticles are not easy to detect, and it is evident that there is high demand in novel techniques for the reliable detection, characterization, sorting, and tracking of nanoscale particles of various sorts. In public health, for example, there is concern about the impact caused by the accelerating rate of nanoparticle emissions and waste. It has been determined that the inhalation of ultrafine particles originating from emissions of various kinds can cause heritable mutations. The development of nanoparticle sensors is also a high priority for environmental monitoring and for the detection of various agents used in biotertorism. Furthermore, as the feature size of integrated circuits becomes increasingly smaller, contamination control of ultrafine particles poses a challenge for the semiconductor industry.

Among the different detection strategies, optical techniques are especially attractive because of their noninvasive nature, high-sensitivity, and potential for realtime detection. Most of the optical schemes rely on the detection of scattered light from an ensemble of particles. However, the detection of single nanoparticles is a challenging task which, so far, has been only accomplished by indirect means, i.e., by fluorescent labeling or immobilization on a surface and subsequent analysis with dark field microscopy. It has been recognized that current real-time single particle detection methods for micrometer-sized particles are not suitable for nanoparticle detection because the intensity of light scattering scales with the sixth power of particle size. This rapid decrease of the signal renders small particles invisible.

Real-time nanoparticle detection demands an interaction mechanism with a weaker dependence on particle size. One strategy in this direction relies on detecting the scattered light interferometrically, thereby accessing the scattered electric field amplitude as opposed to the scattered power. This approach has been demonstrated, almost 20 years ago, in U.S. Pat. Nos. 5,037,202 and 5,061,070, and recently applied for the detection of immobilized gold particles as small as 5 nm in diameter. Other detection schemes with an $r_o^3$ signal dependence ($r_o$=particle radius) aim at measuring particle absorption cross sections by means of the photothermal effect or measuring optical gradient forces acting on nanoparticles in strongly focused laser beams.

Although these methods extend the detection sensitivity to smaller particle sizes, they suffer from other shortcomings which prevent the detection of single nanoparticles in real time. Either they require particle immobilization to ensure sufficiently long acquisition times or they are subject to a background signal originating from Brownian motion or direct detector exposure.

SUMMARY OF THE INVENTION

It is therefore an object of the invention to provide a technique for measuring nanoparticles which overcomes the above-noted shortcomings.

To achieve the above and other objects, the present invention is directed to a background-free detection approach which gives us unsurpassed real-time detection sensitivity for nanoscale particles. We demonstrate the successful detection and classification of low-index particles such as individual viruses carried in a microfluidic system. In the current version, we are able to detect individual water-solubilized polymer particles of 10 nm radius within a few milliseconds. Our detection scheme is well suited for the screening and sorting of various nanoscale particles such as viruses and larger proteins and is compatible with current microfluidic technology.

The present invention provides a background-free real-time detection scheme capable of recognizing low-index nanoparticles such as single viruses in water. The method is based on interferometrically measuring the electromagnetic field amplitude of the scattered light. A split detector is used to generate a background-free signal that renders unprecedented sensitivity for small particles. In its current configuration the sensor is capable of detecting low-index particles in water down to 10 nm in radius or single gold particles as small as 5 nm. We demonstrate the detection of such small particles in a microfluidic system with a time resolution of 1 ms.

The invention provides a background-free, interferometric detection technique for nanoscale particles. The detector works in real time and with single particle sensitivity. Interferometric detection ensures that the signal amplitude scales with the third power of particle size, and the use of a split detector ensures the best possible signal-to-noise ratio, independent of laser power noise. Within a one-millisecond time window we are able to reliably detect a single 10 nm polystyrene particle or a single 5 nm gold particle. Even higher sensitivity could be achieved by modulating the reference beam length (phase modulation) or by heterodyne detection. The detection scheme will find applications in a variety of fields such as particle tracking inside cells, detection of biowarfare agents (viruses), contamination control of water and air, and others. The detector can also be used as a prescreening stage in a larger biodetector assembly for deciding whether a subsequent one-shot detector stage with high chemical specificity (antigenantibody, polymnerase chain reaction, laser spectroscopy, etc.) should be exposed or not.

DESCRIPTION OF THE DRAWINGS

A preferred embodiment of the present invention will be set forth in detail with reference to the drawings, in which.

DETAILED DESCRIPTION OF THE PREFERRED EMBODIMENT

Figure 1:
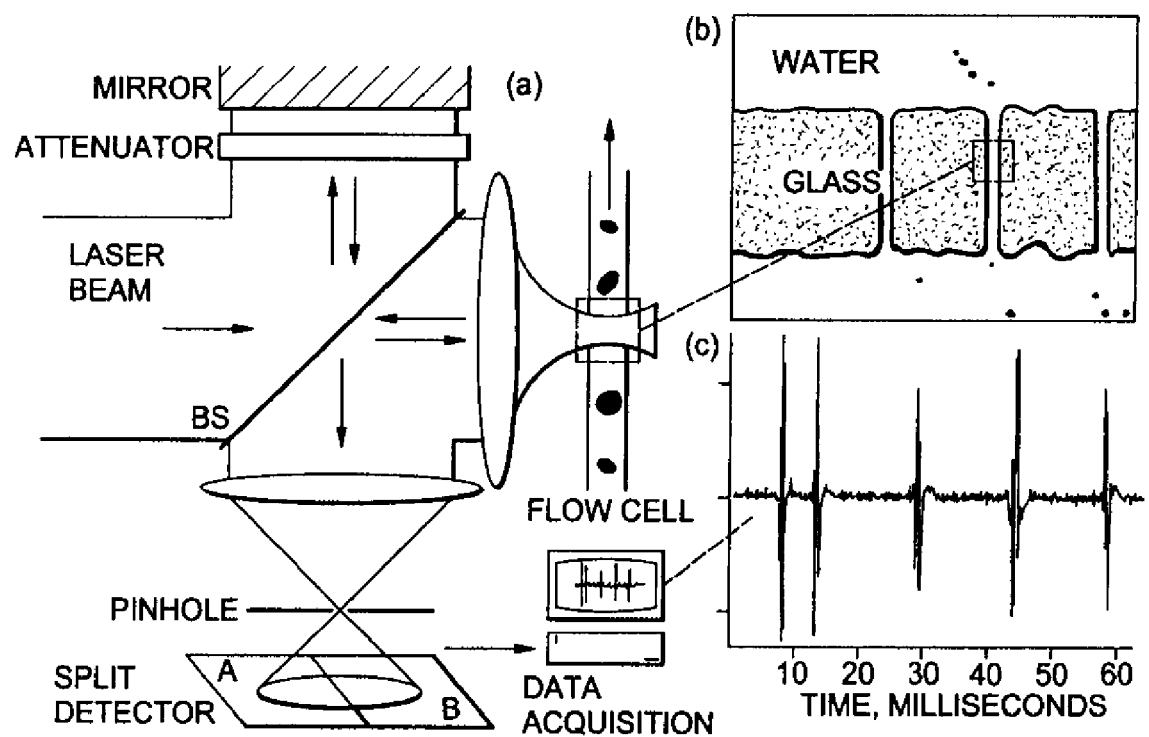
FIG. 1 shows a schematic rendering of the detector according to the preferred embodiment.

A preferred embodiment of the present invention will be set forth in detail with reference to the drawings, in which like reference numerals refer to like elements throughout.

The detection scheme is schematically shown in FIG. 1 as 100. Using the electro-osmotic effect, as shown in FIG. 1, part (b), a particle solution 102 containing particles 104 is transported through a microfluidic channel 106. The channel 106 is subdivided by a barrier 108 with various nanoscale channels 110. As shown in FIG. 1, part (a), a laser source 112 emits a $\lambda=532$ nm laser beam L, which is split by a 50/50 beam splitter 114 into two perpendicular paths $L_1$, $L_2$. One path $L_1$ serves as a reference for later interferometric recombination in a reference arm including an attenuator 116 and a mirror 118, and the other path $L_2$ is focused with an objective lens 120 (NA=1.4) into a single preselected nanochannel. In principle, many channels could be sampled sequentially or in parallel by making use of a programmable spatial light modulator. The lateral dimensions of the nanochannels are comparable to the size of the laser focus, ensuring that no more than one particle crosses the focus at any time. The backscattered light from a particle passing through the laser focus is collected with the same objective lens 120 and is then recombined with the reference beam by the beamsplitter 114 and directed through a lens 122 and a 500 µm pinhole 124 onto a split photodetector 126. The power of the reference beam can be arbitrarily attenuated by the attenuator 116 using a $\lambda/2$ plate placed between two polarizers or by any other suitable attenuation technique. The signal from the detector 126 is analyzed in a data acquisition system 128 in a manner to be described below.

Plot (c) in FIG. 1 shows a typical detector time trace S(t). Each peak represents a single particle passing through the laser focus. Important elements in the preferred embodiment are (i) interferometric detection, (ii) variable attenuation of the reference beam by the attenuator 116, and (iii) the use of a split detector 126 to ensure a background-free signal.

To understand the nature of the detector signal, let us denote the field of the scattered light as $E_s$, and the field of the reference beam as $E_r$. When the particle is in the focus, the intensity distribution on the detector surface is calculated as $$I=|E_r|^2+|E_s|^2+2Re\{E_r^*E_s\} \quad (1)$$

The signal S(t) measured by the split detector corresponds to the difference between two halves of the detector surface normalized by the total power incident on the detector, i.e., $$S = \frac{\left(\int_\subset I da - \int_\supset I da\right)}{\int_O I da},$$

with $\subset$ and $\supset$ denoting the two halves of the photodetector surface and $\circ$ denoting the entire photodetector surface. In the absence of a passing particle, the reference beam and the light backreflected by optical elements are adjusted into the center of the split photodetector such that the differential signal S(t) is zero. The interference between the reference beam and the backreflected light does not affect our detection method because it is stationary and therefore does not generate any differential signal. Thus, S(t) is a background-free signal similar to fluorescence that is commonly used to detect and track single molecules.

When a nanoparticle passes through the nanochannel, the symmetry of the backscattered light is disturbed, and the detector signal S(t) is defined by the interferometric term $$S(t) = 2\text{Re}\left\{\frac{\int_\subset E_r^* E_s da - \int_\supset E_r^* E_s da}{\int_O |E_r|^2 da}\right\}. \quad (2)$$

Here, we neglected the scattered light intensity $|E_s|^2$ in the numerator which is legitimate as long as the reference field is stronger than the scattered field. For the same reason, we only retained the reference beam intensity $|E_r|^2$ in the denominator and rejected all terms in $E_s$. These approximations are justified considering the weak signal scattered by a nanoparticle.

Figure 2:
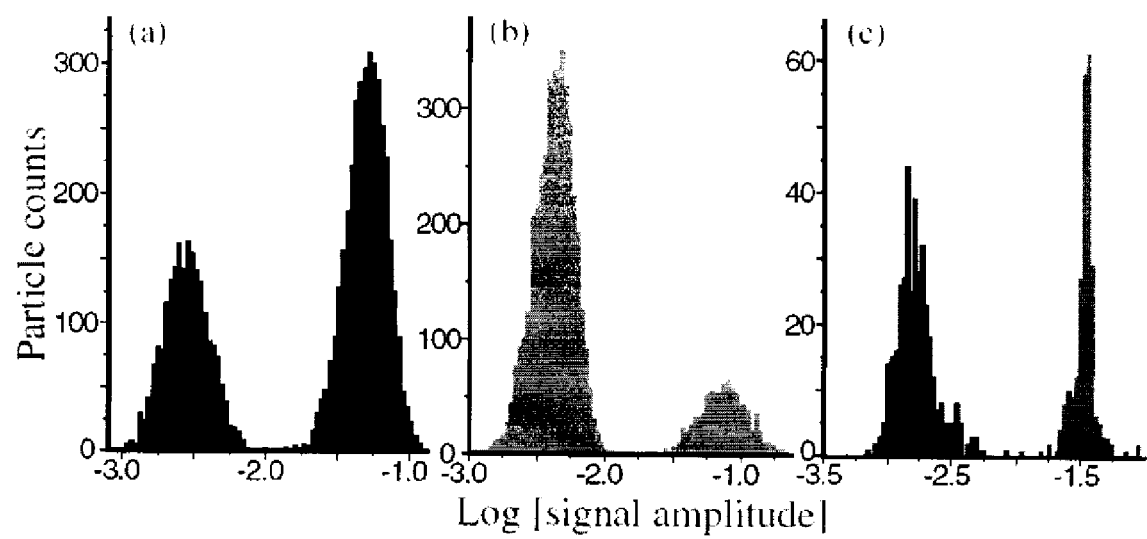
FIG. 2 shows histograms of signal amplitudes obtained with the detector of FIG. 1.

Light scattering from a particle moving through the nanochannel depends on the particle position relative to the center of the laser focus giving rise to a nonzero signal S(t) recorded by the split photodetector. The amplitude of the signal depends on the particle's polarizability which, in turn, depends on particle size and shape, as well as on its dielectric properties. As an example, in FIG. 2, plot (a) shows a histogram of signal amplitudes for a mixture of polystyrene particles of two different sizes, $r_0=15$ nm and $r_0=40$ nm. The distribution shown in FIG. 2, plot (b) corresponds to a mixture $r_0=7$ nm and $r_0=20$ nm gold nanoparticles. The individual particle distributions appear clearly resolved, which demonstrates that our detection strategy is well suited for characterization and subsequent separation on a particle by particle basis. Similar procedures can be applied to separate biological particles, such as viruses or bacteria. In fact, we are currently able to detect single Influenza A X-31 viruses in real time and discriminate them from other particles of similar size. FIG. 2, plot (c), shows a histogram of signal amplitudes for a mixture of that virus (left peak) and 100 nm polystyrene beads. All data sets have been acquired in water with each individual detection event lasting approximately 1 ms.

To quantitatively understand the sensitivity and detection limits, we first note that, for a given instant of time, the signal S(t) in Eq. (2) depends linearly on the electric field amplitude $E_s$ of the scattered light. On the other hand, the scattered field is linearly related to the amplitude of the focused laser field $E_f$ and the particle polarizability $\alpha$. Hence, the detector signal satisfies the following proportionality:

$$S(t) \propto Re(\alpha)\sqrt{P_f/P_r}, \quad (3)$$

where $P_f$ and $P_r$ are the powers of the focused laser beam and the reference beam, respectively. The proportionality constant depends on the momentary particle position, on the result of spatial integrations, on various physical constants, and on experimental conditions such as the numerical aperture of the objective, mirror reflectivity, detector quantum efficiency, etc. An important fact is that $P_f$ and $P_r$ are independent from each other. Thus the total incident laser power can be increased and focused to a more intense spot while the reference beam can be attenuated, thereby increasing the differential signal amplitude $S(t)$ and allowing even smaller particles to be detected.

Figure 3:
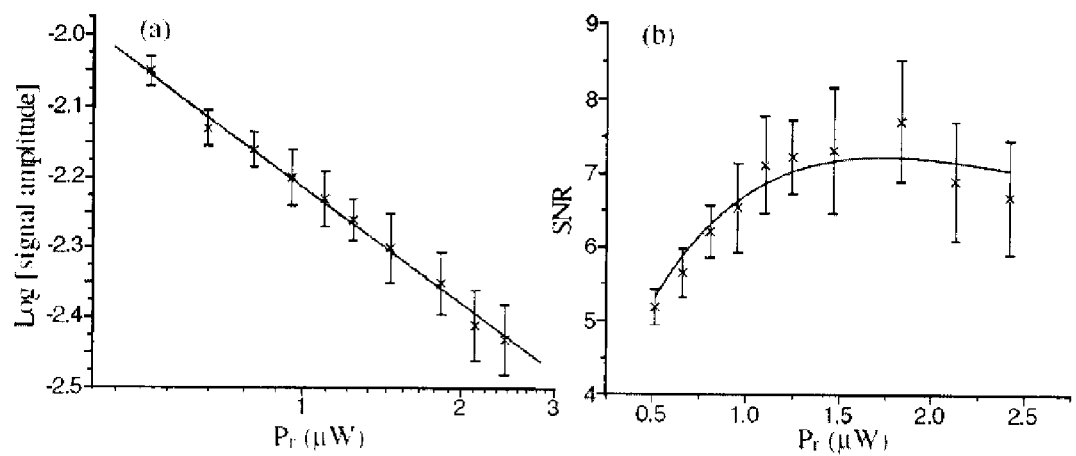
FIG. 3 shows an experimental analysis of detection limits.

FIG. 3, plot (a) demonstrates this property for a sample with $r_0 = 50$ nm polystyrene particles. The plot shows the dependence of the signal amplitude $S(t)$ on the reference beam power $P_r$. The red line is a fit according to Equation (3). The detector signal increases the more the reference beam is attenuated.

In order to assess the detection limit, we analyze the signal-to-noise ratio (SNR). The noise floor of the detector signal is defined in the absence of the scattered field. Since the spot of the reference beam is positioned at the center of the split photodetector, the signal noise does not depend on power noise of the laser. Instead, it is defined by the beam pointing instability and electronic noise of the detector. The pointing instability causes the beam spot to deviate from its central position on the detector, giving rise to a nonzero detector response. Denoting the beam angle with respect to the unperturbed optical axis as $\theta$, the noise level for the differential signal can be expressed as $$N = \sqrt{P_v^2 + [\theta_{rms} P_r]^2}/P_r, \quad (4)$$

where $P_v$ represents the "power equivalent" of electronic detector noise and $\theta_{rms} P_r$ accounts for the pointing instability of the laser. When $P_r \gg P_v$, the noise becomes constant and proportional to $\theta_{rms}$. However, when $P_r$ is attenuated such that $\theta_{rms} P_r$ is less than or approximately equal to $P_v$, the noise level increases rapidly with decreasing $P_r$. Using Equations (3) and (4), we obtain:

$$\frac{S}{N} \propto Re(\alpha) \sqrt{\frac{P_f P_r}{P_v^2 + [\theta_{rms} P_r]^2}}, \quad (5)$$

which predicts that the best SNR is achieved when the power of the reference beam is $$P_r^{max} = P_v/\theta_{rms}.$$

FIG. 3, plot (b) shows the measured average SNR for 50 nm particles for different reference beam powers $P_r$. The plot shows the dependence of the SNR on the reference beam power. The curve is a fit according to Eq. (5) and demonstrates that the SNR has a maximum as predicted by Eq. (5). The measured detector noise equivalent power is $P_v = 0.7$ nW (rms), and the laser pointing instability is $\theta = 4.5 \times 10^{-4}$ (rms). Those values predict a maximum at $P_r = 1.6$ µW, which is in agreement with the fitted curve in plot (b). Several hundred particles were used for each data point. It turns out that the recipe for achieving the best sensitivity and lowest detection limit is to increase the laser power while keeping the reference beam at the level of maximum SNR.

The lowest possible reference beam power is determined by the backscattered light in the absence of a passing particle. This backscattered light is due to the optical index mismatch between the different interfaces and is analogous to background fluorescence in single molecule experiments. Because this backscattered light interferes with the scattered light from a passing particle it assumes a similar function as the reference beam. When this unwanted backscattering becomes stronger than the reference beam power we may simply replace $P_r$ in Eq. (5) by the power of the backscattered light $P_b$ and obtain the following limit;

$$Max[S/N] \propto Re(\alpha)\sqrt{P_f/P_b}/\theta_{rms} = Re(\alpha) \times \sqrt{R}/\theta_{rms};$$

where, in the last step, we expressed the backscattered light by the focused beam power $P_f$ using a generalized reflectivity R. Thus, the best possible SNR in our detection scheme is entirely defined by the index mismatch between the interfaces and the beam pointing instability. Both effects can be minimized in a favorably engineered detector design.

Let us now compare the SNR of our detection scheme with the SNR of standard scattering-based detection. According to Eq. (2), the maximum normalized differential signal amplitude ($S=1$) is obtained when the phase between $E_s$ and $E_r$ (or $E_b$) assumes a value which concentrates all energy on one half of the split detector. This can only happen if the scattered field amplitude is equal to the amplitude of the reference beam or, equivalently, to the amplitude of the backscattered beam, i.e., $P_s = P_b$. For sufficiently strong powers our SNR becomes $$\{S/N\}_{preferred\ embodiment} = (1/\theta_{rms})\sqrt{P_s/P_b}.$$

On the other hand, the maximum SNR in standard light scattering can be written as $$\{S/N\}_{scattering} = (1/\eta) P_s/P_b,$$

where $\eta = \sqrt{\langle dP\rangle}/P$ is the laser power noise. The SNR in our detection scheme is proportional to $\sqrt{P_s/P_b}$, versus $P_s/P_b$ for scattering-based detection, and therefore proportional to the third power of particle size, versus the sixth power of particle size for scattering-based approaches. Second, the SNR in light scattering depends on laser power noise which cannot easily be controlled. On the other hand, our scheme depends on the angular pointing stability of the laser which can be controlled, for example, by reducing the optical path length. Furthermore, the dimensionless pointing stability coefficient $\theta_{rms}$ for lasers is much smaller (by orders of magnitude) than typical power noise.

Figure 4:
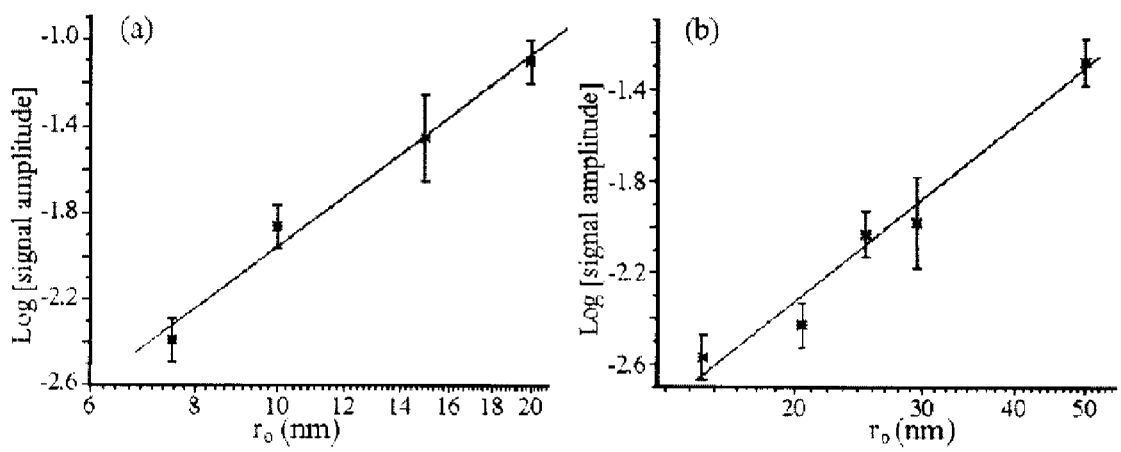
FIG. 4 shows dependence of the signal amplitude on particle radius.

In order to verify the $r_0^3$ dependence we measured the signal amplitudes of monodisperse particles of different sizes. As shown in FIG. 4, we obtain very good agreement with theory for both polystyrene and gold particles. In that figure, plot (a) shows the dependence of the signal amplitude on particle radius $r_0$ for gold particles, while plot (b) shows the same dependence for polystyrene particles in water. The line in both plots is a fit according to $r_0^n$ with $n = 2.9 \pm 0.3$ in plot (a) and $2.6 \pm 0.3$ in plot (b). The threshold for the smallest particle that can be detected is defined by the choice of the minimum acceptable SNR. As demonstrated in FIG. 2, we can reliably detect $r_0 = 15$ nm polystyrene particles and 7.5 nm gold particles in water using a SNR of 3 and a detection bandwidth of $B \approx 10$ kHz (one detection event $\approx 1$ ms). By choosing a more compact design, better index matching at interfaces, and more stable laser sources we expect to considerably increase the detection thresholds.

While a preferred embodiment of the invention has been set forth above, those skilled in the art who have reviewed the present disclosure will readily appreciate that other embodiments can be realized within the scope of the invention. For example, numerical values are illustrative rather than limiting, as are specific techniques for attenuation and the like. Therefore, the present invention should be construed as limited only by the appended claims.

We claim:

1. A method for detecting a particle in a location, the method comprising:
   (a) emitting a beam of electromagnetic radiation;
   (b) splitting the beam of electromagnetic radiation into a first component and a second component;
   (c) directing the first component into a reference arm;
   (d) directing the second component into the location;
   (e) receiving light backscattered from the location;
   (f) causing the backscattered light to interfere with the first component from the reference arm to produce an interference intensity distribution;
   (g) causing the interference intensity distribution to be incident on a detector comprising a plurality of components such that the components detect different spatial components of the interference intensity distribution and detecting the interference intensity distribution with a detector comprising a plurality of components; and
   (h) detecting the particle in accordance with a difference among detection signals from the plurality of components, wherein step (h) comprises determining a size of the particle.

2. The method of claim 1, wherein the difference among the detection signals is a power of a radius of the particle.

3. The method of claim 2, wherein the power is third power or lower.

4. A method for detecting a particle in a location, the method comprising:
   (a) emitting a beam of electromagnetic radiation;
   (b) splitting the beam of electromagnetic radiation into a first component and a second component;
   (c) directing the first component into a reference arm;
   (d) directing the second component into the location;
   (e) receiving light backscattered from the location;
   (f) causing the backscattered light to interfere with the first component from the reference arm to produce an interference intensity distribution;
   (g) causing the interference intensity distribution to be incident on a detector comprising a plurality of components such that the components detect different spatial components of the interference intensity distribution and detecting the interference intensity distribution with a detector comprising a plurality of components; and
   (h) detecting the particle in accordance with a difference among detection signals from the plurality of components, wherein step (h) is performed using an optical force on the particle.

5. A method for detecting a particle in a location, the method comprising:
   (a) emitting a beam of electromagnetic radiation;
   (b) splitting the beam of electromagnetic radiation into a first component and a second component;
   (c) directing the first component into a reference arm;
   (d) directing the second component into the location;
   (e) receiving light backscattered from the location;
   (f) causing the backscattered light to interfere with the first component from the reference arm to produce an interference intensity distribution;
   (g) causing the interference intensity distribution to be incident on a detector comprising a plurality of components; and
   (h) detecting the particle and a size of the particle in accordance with a difference among detection signals from the plurality of components.

6. The method of claim 5, wherein the difference among the detection signals is a power of a radius of the particle.

7. The method of claim 6, wherein the power is third power or lower.

8. The method of claim 5, wherein step (h) is performed using an optical force on the particle.

* * * * *